(12) United States Patent
Solomon et al.

(10) Patent No.: US 6,200,338 B1
(45) Date of Patent: Mar. 13, 2001

(54) ENHANCED RADIOPACITY OF PERIPHERAL AND CENTRAL CATHETER TUBING

(75) Inventors: Donald D. Solomon, Southlake; Fidelis C. Onwumere, Mansfield, both of TX (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/224,443

(22) Filed: Dec. 31, 1998

(51) Int. Cl.$^7$ .................. A61F 2/04; A61F 2/06; A61L 29/00; A61M 25/095
(52) U.S. Cl. .............. 623/1.34; 623/23.58; 428/36.9
(58) Field of Search ................... 623/1.34, 921, 623/23.58; 600/36; 428/35.7, 36.9

(56) References Cited

U.S. PATENT DOCUMENTS

| | | |
|---|---|---|
| 3,336,918 | 8/1967 | Jeckel . |
| 3,618,614 | 11/1971 | Flynn . |
| 3,749,134 | 7/1973 | Slingluff et al. . |
| 3,901,829 | 8/1975 | Slingluff et al. . |
| 4,182,787 | 1/1980 | Goossens et al. . |
| 4,282,876 | 8/1981 | Flynn . |
| 4,722,344 | 2/1988 | Cambron et al. . |
| 5,177,170 | 1/1993 | Sarpeshkar et al. . |
| 5,289,831 | * 3/1994 | Bosley .................... 623/12 |
| 5,346,981 | 9/1994 | Sarpeshkar et al. . |

* cited by examiner

Primary Examiner—David H. Willse
Assistant Examiner—Choon P. Koh
(74) Attorney, Agent, or Firm—Blakey, Sokoloff, Taylor & Zafman

(57) ABSTRACT

A medical implant, tubing and method to provide enhanced X-ray detection intensity in catheters, stents, vascular grafts or other tubular implants. In one aspect the medical implant includes a visually transparent radiopaque polymer and a filler material having a radiopaque component.

27 Claims, 1 Drawing Sheet

ENHANCED RADIOPACITY OF
PERIPHERAL AND CENTRAL CATHETER
TUBING

BACKGROUND OF THE INVENTION

1. Field of the Invention

The invention relates generally to medical implants and more particularly to medical implants including medical tubing for catheters, stents, and other devices.

2. Background of the Invention

In certain medical procedures, medical implants are placed into the body. These implants include catheters inserted into body passages, vessels, or cavities for passing fluids, draining fluids, making examinations, etc. A stent is a second type of medical implant used to maintain a body orifice or cavity during skin grafting or to provide support for tubular structures, for example, during or after anastomosis.

It is generally desirable that medical implants, such as catheters and stents, be radiographically opaque such that their precise location within the host body can be detected by X-ray examination. In addition, it is advantageous that such medical implant be optically or visually transparent so that a flow of fluid therethrough may be observed.

Many tubular-shaped medical implants, such as catheters and stents are made from a polymer base. Suitable polymers are those that can be formed into tubular shapes that are, particularly in the case of catheters, flexible enough to be routed or snaked to a location in the body. In the case of a peripherally inserted central catheter (PICC), for example, the tubing of the catheter is routed or snaked, in one instance, through a vein in a patient's arm or neck to the superior vena cava of the patient's heart. The tubing should be flexible enough to be routed in this manner without causing trauma to the patient. The polymer chosen as the medical implant should also have sufficient strength when formed into a tubing so that the lumen does not collapse in a passageway or orifice. Still further, the tubing should be resistant to crimping or kinking so that a continuous passageway is assured. Polyurethane-based polymers are a popular choice for medical implant polymers, because certain polyurethanes possess the noted beneficial properties.

In general, polyurethanes are condensation products of reactions between diisocyanate (isocyanate compounds having a functionality of two) and soft-block polyols. Typically, polyurethanes are combined with low molecular weight aliphatic or aromatic diols or diamines as chain extenders to impart the useful properties of flexibility, strength, and kink resistance. Low molecular weight diols include butane diol, pentane diol, hexane diol, heptane diol, benzene dimethanol, hydraquinone diethanol and ethylene glycol. The addition of diamine chain extenders form a class of polyurethanes commonly referred to as polyurethaneureas. Suitable diamines include ethylene diamine, butanediamine, propane diamine and pentanediamine. An added feature of the polyurethanes with the diol or diamine chain extenders is that catheters or stents formed from these materials are typically optically or visually transparent making these polymer matrices excellent compounds for medical implants. Unfortunately, however, these polyurethanes are generally not radiopaque.

Radiopaque medical implants such as catheters, including radiopaque polyurethanes, have been developed. These radiopaque polymer structures are generally of two forms. A first form of radiopaque polymer incorporates a radiopaque filler or pigment. Typical filler materials include barium sulfate (BaSO4), bismuth subcarbonate, or certain metals such as tungsten (W). Other radiopaque fillers are pigments for incorporation into a polymer tube including bismuth oxychloride and other bismuth salts such as bismuth subnitrate and bismuthoxide (See U.S. Pat. No. 3,618,614). A drawback of the filler incorporated polymers is, although such polymers are radiopaque, the filler tends to make the polymer non-transparent.

A second form of radiopaque polymer useful in medical implants incorporates a halogenated-chain extender into the polymer matrix. Examples of these types of polymers are described in U.S. Pat. Nos. 4,722,344; 5,177,170; and 5,346,981. The preferred halogen in these patents is bromine (Br). Polymers incorporating a brominated-chain extender into the polymer matrix generally yield a tubing that is radiopaque and optically or visually transparent.

In order to impart useful radiopaque properties, the halogenated-chain extended polymer, such as a bromine-chain extended polymer, must have a minimum amount of halogen (e.g., bromine) to impart radiopacity to the polymer. Experimental studies show that the minimum amount of bromine, for example, in a polyurethane-based polymer useful as a catheter, is approximately 15 percent. Amounts less than this tend to make the tubing difficult to detect by X-ray.

A second problem with halogenated-chain extended polymers is the maximum amount of halogen that can be incorporated into the polymer is limited. Experimental studies have shown that polymers having, for example, a bromine concentration greater than 30 percent are too stiff for use as a medical implant, such as a catheter tubing. Accordingly, the radiopacity of the tubing is limited by the amount of bromine that may be incorporated in the polymer matrix without degrading the properties of the tubing made from such a polymer.

As noted above, certain halogenated-chain extended polymers offer both radiopacity and optical transparency. However, in order to maintain the superior properties demonstrated by conventional thermoplastic polyurethane elastomer with non-halogenated-chain extenders, the amounts of halogen must be strictly limited. It would be desirable, in certain instances, to have a halogenated-chain extended polymer with a radiopaque property that is not limited by the amount of bromine that is incorporated into the polymer matrix. What is needed is a combination that can maximize the radiopacity of the implant without increasing the halogen concentration of the polymer beyond that which would negatively effect the physical characteristics of the medical implant.

BRIEF SUMMARY OF THE INVENTION

A method and apparatus to provide enhanced radiopacity for a polymer while retaining its desirable flexibility or stiffness. In one embodiment, a medical implant such as a tubing is produced comprising a visually transparent radiopaque polymer and a radiopacifying filler material having a radiopaque component.

DETAILED DESCRIPTION OF THE INVENTION

In producing medical implants, catheters, stents, vascular grafts and the like, striking a balance between radiopacity, optical transparency and the supple or flexible properties of the composition to form an effective material is important. The zero-sum nature of increasing one of these properties at the potential expense of another is clear from the background and the prior art, presenting significant limitations.

The invention relates to a radiopaque tubing comprising a visually transparent radiopaque polymer and a radiopaque filler material useful as a medical implant such as a catheter, stent, vascular graft or similar device. In one embodiment, the visually transparent radiopaque polymer comprises a polyurethane including a diisocyanate, a polyol, and a chain extender, which contain between 10–30% by weight bromine concentration. The filler material contains a radiopaque agent which may be, for example, barium sulfate, bismuth subcarbonate, tungsten or other material.

Figure 1:
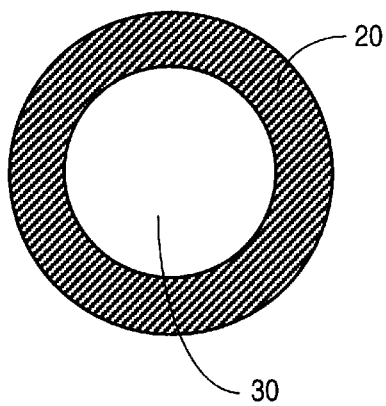
FIGS. 1, 2, 3 and 4 are cross sections of the tubing of alternative embodiments of the invention.

In one embodiment, the filler material is combined with the radiopaque polymer in a tubing by combining filler and polymer and extruding them within a unitary tubing. FIG. 1 shows a cross section of a tubing wherein the combination of radiopaque polymer and filler material is disposed circumferentially to form the tubing 20 defining the lumen 30. In one embodiment, the filler material is filler of, for example, barium sulfate or bismuth subcarbonate, that provides radiopacity to the final apparatus (e.g., tubing). One way to make a medical implant such as medical tubing is to combine the filler as a powder with transparent radiopaque polymer chips and process the combination through a twin screw extruder to form pellets. The pellets are then extruded according to conventional extrusion techniques to form the medical implant shown in FIG. 1.

In another embodiment, the filler material includes filler and polymer (e.g., thermoplastic polyurethane) and is co-extruded with an amount of visually transparent radiopaque polymer. The tubing of FIG. 1 may be extruded from polymer pellets containing the filler material (filled polymer) and polymer pellets containing the visually transparent radiopaque polymer using one extruder. To make polymer pellets of the filler material, the filler (e.g., barium sulfate, bismuth subcarbonate, etc.) may be added in the form of a powder with polymer chips and processed through a twin screw extruder to form the filled polymer pellets.

Figure 2:
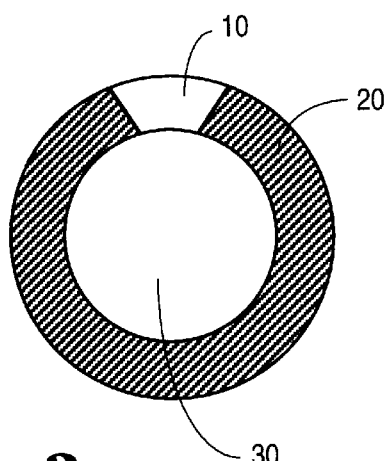
Figure 3:
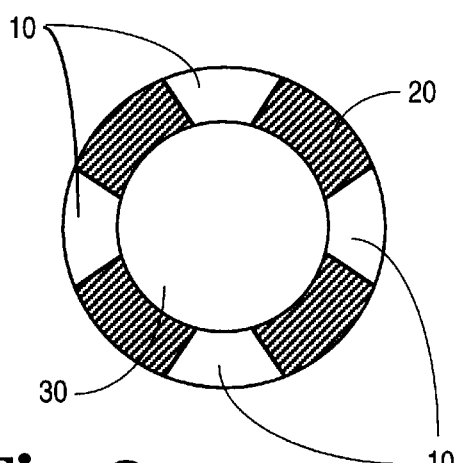
Figure 4:
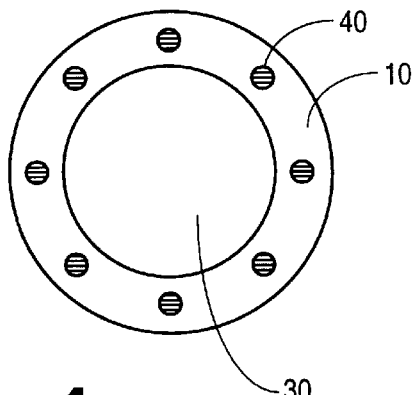

While providing the advantage of substantial increases in radiopacity, when combined with the polymer, the filler material in the resulting tubing of the invention will tend to limit optical transparency of the polymer. This can be overcome through various embodiments which provide at least one window of visually transparent radiopaque polymer, which is free of filler material, co-extruded to produce an optically or visually clear cross-sectional segment of the tubing. FIGS. 2–4 illustrate various embodiments formed by combining visually transparent radiopaque polymer (e.g., brominated polyurethane) with a filler material of a filled polymer (e.g., filled thermoplastic polyurethane and/or filled brominated polyurethane).

FIG. 2 shows a cross-section of tubing having filler material (filled polymer) disposed throughout the tubing 20. A visually transparent radiopaque polymer window is co-extruded as segment 10 allowing for visually observing the fluid flowing within the tubing lumen 30. In other embodiments, multiple windows may be added where desired in segments spaced apart along the cross sectional circumference of the tubing, yet extending longitudinally, parallel to the general flow direction within the lumen. Such an example of multiple window composition is illustrated in FIG. 3.

Each embodiment illustrated by FIG. 2 and FIG. 3 may be co-extruded using two extruders, one extruder for the visually transparent radiopaque polymer and a second extruder for the filler material, which, in these embodiments, is a filled polymer. In FIG. 3, the particular extrusion may be split to form the multiple windows appearing longitudinally as stripes along the length of the tubing. It is appreciated that additional embodiments of various window dispositions are within the scope and contemplation of the invention.

FIG. 4 shows an embodiment resulting from co-extrusion of the visually transparent radiopaque polymer having no filler material and the filler material (filled polymer. In FIG. 4, the filler material (filled polymer) is largely isolated and concentrated in one or more segments 40 disposed within the otherwise visually clear tubing of, for example, brominated polymer 10. When the tubing is viewed lengthwise, the segments 40 of filler material tend to form one or more stripes of varying size which extend generally longitudinally along some extent of the tubing, basically parallel to the flow direction within the lumen 30. This embodiment allows the specific placement of radiopaque, yet potentially optically obstructing segments (filled polymer) so as to allow observation of fluid flow while retaining the superior radiopacity of the segments, appearing as stripes within the tubing, wherein concentrated amounts of filler material are disposed. As with the embodiment of FIG. 3, a co-extrusion using two extruders with split extrusions may form the striped pattern.

The visually transparent radiopaque polymer is prepared according to polymerization procedures known in the art. In certain embodiments, the polymer is a brominated polyurethane prepared according to methods described in U.S. Pat. Nos. 5,346,981, 5,177,170 and 4,722,344. One example of a suitable polyurethane comprises a diisocyanate, a polyol, and a brominated chain extender. Suitable diisocyanates include, but are not limited to, trans-1,4-cyclohexanediisocyanate, methylene bis-diphenyl diisocyanate, and, methylene bis-dicyclohexanediisocyanate. Suitable polyols include but are not limited to polytetrahydrafuran, polyethyleneglycol, ethyleneglycol-b-proyleneglycol-b-ethyleneglycol, polyesterdiol and polyestercarbonate diol.

Suitable brominated chain extenders include, but are not limited to, bromobisphenol A- diethanol (e.g. tetrabromobisphenol A- diethanol), brominated hydroquinone diethanol, brominated benzene diethanol and brominated bipheyloxydiethanol. Where the visually transparent radiopaque polymer is a polyurethane, the bromine concentration in the polymer is typically less than about 30 percent by weight of the polymer due to the potential effect higher levels of bromine have on the properties of the polymer, and potential stoichiometric limitations of attaching additional bromine to the polymer.

Suitable filler for the filler material of the medical implant of the invention include, but are not limited to, barium sulfate, certain bismuth compounds including bismuth subcarbonate and bismuth oxychloride, and certain metals that have radiopaque properties including tungsten. As noted above, suitable fillers may be combined directly with the visually transparent radiopaque polymer (e.g., thermoplastic polyurethane containing bromine chain extenders) to form the tubing shown, for example, in FIG. 1. Alternatively, suitable fillers may be combined with a radiopaque or a non-radiopaque polymer to form a filled polymer. The filled polymer may then be combined with a visually transparent radiopaque polymer to form the tubing shown, for example in FIGS. 1–4. Suitable non-radiopaque polymers for filler material include, but are not limited to, the thermoplastic polyurethanes noted above with desired elastomeric properties (e.g., polyurethanes, or polyurethaneurea, chain extended with low molecular weight diols or diamines respectively). Suitable radiopaque polymers include, but are not limited to, the polyurethanes having brominated chain extenders such as described above with reference to the visually transparent radiopaque polymer.

In particular embodiments where the visually transparent radiopaque polymer is a brominated polyurethane and is combined with a filler material of filled radiopaque or non-radiopaque polyurethane, a resulting medical implant that is tubing will have a percent filler material (i.e., filled polyurethane) of between 35% and 65%, by weight. Typical weight ratios of brominated polyurethane to filled polyurethane include 50:50, 55:45, 60:40, 65:35. It is to appreciated that the weight ratios will vary depending on, among other considerations, the desired level of radiopacity of the resulting medical implant and whether the filled polymer is formed of a radiopaque polymer.

The addition of the radiopacifying filler material (either as filler alone with the visually transparent radiopaque polymer or as filler combined with a radiopaque or non-radiopaque polymer) substantially increases the X-ray intensity of the resulting tubing without affecting the properties of the polymer. Its flexibility and other elastomeric properties are generally preserved. Typical proportions of filler used vary depending on the particular type. For bismuth subcarbonate, for example, the percentage of filler by weight to the entire tubing is between 15 and 30% when combined with a polyurethane polymer. Barium sulfate may be utilized in a concentration of between 18–35%, although, in certain coextrusion procedures, this may be increased up to 45%. Tungsten radiopacifying filler material is ordinarily employed in a percentage concentration by weight of the tubing of between 15–25%.

The preceding detailed description focused on the combination of a polymer and a filler material. It is to be appreciated that additional polymers or additives, for that matter, may be combined with the polymer and the filler material to, in certain instances, further enhance the properties of the ultimate composition including a medical implant. For example, polyurethane can be combined with other medical grade polymers such as polyether amide, polyether ester, and non-urethane-based thermoplastic elastomers.

In the preceding detailed description, the invention is described with reference to specific embodiments thereof. It will, however, be evident that various modifications and changes may be made thereto without departing from the broader spirit and scope of the invention as set forth in the claims. The specification and drawings are, accordingly, to be regarded in an illustrative rather than a restrictive sense.

What is claimed is:

1. A medical implant comprising:
    a first visually transparent radiopaque polymer; and
    a second polymer comprising filler material having a radiopaque component.

2. The medical implant of claim 1, wherein the second polymer is brominated.

3. The medical implant of claim 1, wherein the filler material comprises filler selected from the group consisting of barium sulfate, bismuth subcarbonate and tungsten.

4. The medical implant of claim 1 wherein the first polymer is a polyurethane.

5. The medical implant of claim 1 wherein the first polymer comprises a polyol.

6. The medical implant of claim 1 wherein the first polymer comprises an isocyanate-reactive brominated chain extender.

7. The medical implant of claim 6 wherein the bromine concentration is between about 10% and 30%, by weight of the medical implant.

8. The medical implant of claim 1 wherein the filler material is barium sulfate in a range between about 18% to 45%, by weight of the medical implant.

9. The medical implant of claim 1 wherein the filler material radiopaque component is a bismuth compound in a range between about 15% to 30%, by weight of the medical implant.

10. The medical implant of claim 1 wherein the filler material radiopaque component is tungsten in a range between about 15% to 25%, by weight of the medical implant.

11. A tubing comprising:
    a first visually transparent radiopaque polymer; and
    a second polymer comprising radiopacifying filler material having a radiopaque component.

12. The tubing of claim 11, wherein the second polymer is brominated.

13. The tubing of claim 11 wherein the filler material comprises filler selected from the group consisting of barium sulfate, bismuth subcarbonate and tungsten.

14. The tubing of claim 11 wherein the polymer is a polyurethane.

15. The tubing of claim 11 wherein the polymer comprises a polyol.

16. The tubing of claim 11 wherein the polymer comprises an isocyanate-reactive brominated chain extender.

17. The tubing of claim 16 wherein the bromine concentration is between about 10% and 30%, by weight of the tubing.

18. The tubing of claim 11 wherein the filler material radiopaque component is barium sulfate in a range between about 18% to 45%, by weight of the tubing.

19. The tubing of claim 11 wherein the filler material radiopaque component is a bismuth compound in a range between about 15% to 30%, by weight of the tubing.

20. The tubing of claim 11 wherein the filler material radiopaque component is tungsten in a range between about 15% to 25%, by weight of the tubing.

21. A method comprising:
    combining a visually transparent, radiopaque first polymer and a second polymer comprising a radiopaque filler material; and
    forming the combination into a medical implant.

22. The method of claim 21, wherein the second polymer is brominated.

23. The method of claim 21, wherein the visually transparent radiopaque polymer is a brominated radiopaque polyurethane.

24. The method of claim 21, wherein the polymer is a first portion and a second portion and the method further comprises:
    co-extruding a second portion of the polymer.

25. The method of claim 21, wherein the polymer is a first portion and a second portion and the method further comprises:
    co-extruding a second portion of the polymer so as to substantially isolate and encompass at least one segment of the polymer-filler material combination within the polymer.

26. The method of claim 24, wherein the step of co-extruding further comprises forming a tubing wherein the polymer-filler combination is disposed longitudinally with a portion of the tubing.

27. The method of claim 26, wherein the longitudinal disposition of first portion polymer-filler combination form stripes co-extensive with a portion of the tubing.

* * * * *